United States Patent
Babaev

(10) Patent No.: US 8,376,970 B2
(45) Date of Patent: Feb. 19, 2013

(54) ULTRASOUND APPARATUS AND METHODS FOR MITIGATION OF NEUROLOGICAL DAMAGE

(76) Inventor: Eilaz Babaev, Minnetonka, MN (US)

( * ) Notice: Subject to any disclaimer, the term of this patent is extended or adjusted under 35 U.S.C. 154(b) by 460 days.

(21) Appl. No.: 12/608,030

(22) Filed: Oct. 29, 2009

(65) Prior Publication Data
US 2011/0105958 A1    May 5, 2011

(51) Int. Cl.
*A61H 23/00* (2006.01)
(52) U.S. Cl. .......................................................... 601/2
(58) Field of Classification Search ........ 601/2; 604/22, 604/19; 606/60, 246, 279; 128/898
See application file for complete search history.

(56) References Cited

U.S. PATENT DOCUMENTS

| | | | |
|---|---|---|---|
| 7,662,177 B2 * | 2/2010 | Babaev | 607/96 |
| 2005/0049525 A1 * | 3/2005 | Yamada et al. | 601/2 |
| 2008/0119779 A1 * | 5/2008 | Babaev | 604/22 |
| 2009/0163836 A1 * | 6/2009 | Sliwa | 601/2 |
| 2010/0076349 A1 * | 3/2010 | Babaev | 601/2 |

OTHER PUBLICATIONS

Raso et al. Can therapeutic ultrasound influence the regeneration of peripheral nerves? Journal of Neuroscience Methods. 142(2):185-102. Mar. 30, 2005.*

* cited by examiner

*Primary Examiner* — Parikha Mehta

(57) ABSTRACT

This invention discloses methods and devices using ultrasound energy for use before, during or after surgery for providing a therapeutic effect on nerve tissue. The disclosure describes the use of ultrasound devices consisting of an ultrasound generator, ultrasound transducer and ultrasound horn at least partially enclosed by a shield to enhance neurogenesis on neurons of the central nervous system and other nerve tissue. The shield allows the application of therapeutic levels of ultrasound to nerve tissue to enhance the regeneration of the nerve tissue and mitigate damage to the nerve tissue. The shield serves to protect patient from unwanted contact with portions of the ultrasound horn not being utilized for therapeutic effect. The ultrasound application may be included in devices that have other uses such as a cutting edge for removing tissue.

15 Claims, 6 Drawing Sheets

ULTRASOUND APPARATUS AND METHODS FOR MITIGATION OF NEUROLOGICAL DAMAGE

BACKGROUND OF THE INVENTION

Back pain may affect 80% of certain populations at some time in their lives. It comes in many forms, from lower, middle, or upper back pain to low back pain with sciatica. Common back pain causes include trauma injury, birth defects, tumors, nerve and muscular problems, degenerative disc disease, and arthritis. It is estimated that from 1 to 10% of back pain suffers may require surgery to attempt to relieve the problem.

Examples of specific causes of back pain that may result in surgery being required include: bulging or ruptured disks, sciatica, osteoarthritis, spinal stenosis, scoliosis and osteoporosis. Although the physical cause of the back pain itself may have injured the nerve tissue within and near the spine prior to surgical relief. Even though surgery is typically intended to relieve the cause of the pain, the surgery may itself damage the nerves which are longitudinally within and laterally disposed throughout the spinal column along with non-neural tissue such as; muscle, bone, ligaments, blood vessels and other tissues. Although non-neural tissue tends to regrow with time, nerves of the central nervous system spinal column generally do not regrow or repair.

Injury to the spinal cord or central nervous system can be one of the most devastating and disabling injuries possible. Depending upon the severity of the injury, paralysis of varying degrees can result. Paraplegia and quadriplegia often result from severe injury to the spinal cord.

Damage of the peripheral nervous system damage has been known to heal, although at a very slow rate, in adults. It had been long thought that once damaged, the nerves in adults of the central nervous system do not regenerate and cannot be caused to regenerate within the environment of the central nervous system. Any regeneration of injured nerves in the central nervous system of mammals had been found to occur, if at all, only within a very short period immediately after the injury occurs. After this short period expires, such nerves have not been found to regenerate.

Ongoing efforts in several technological fields are being made to find treatments to repair damaged nerves particularly of the central nervous system.

Electrical stimulation is used to stimulate nerve cell regeneration. For example, stimulating regeneration and repair of damaged spinal nerves through electrodes delivering direct current intravertebrally proximal to the site of spinal nerve injury has been described. US App. No. 20060167527 by Femano. In addition, U.S. Pat. No. 4,919,140 by Borgens et al., describes applying an oscillating electrical field to the central nervous system to regenerate nerve cells. These devices have the drawback of generally require long term implantation within the patient's body.

Additional work is being done on finding ways to block proteins that inhibit nerve repair in adults or administer agents to enhance the regeneration of neuron cells. For example, U.S. Pat. No. 6,776,984 by Schwartz discloses a method of treatment of degenerative neurologic diseases provides for the administration of therapeutically effective amounts of an enhancement agent, such as thrombopoietin, to enhance the regeneration of neuron cells. In addition, work is ongoing to stimulate nerve regeneration in mice with damaged optic nerves by turning off proteins that keep adult nerve cells from growing. However, these therapeutic agents generally are not specific with regard to neuron cells, also having impacts on other tissues creating unwanted side effects throughout a patient's body.

SUMMARY OF THE INVENTION

This disclosure is for a method and apparatus using ultrasound energy for mitigating neurological damage to nerve tissue during surgery and/or providing a therapeutic effect to assist regeneration of nerve tissue. The use of ultrasound devices for surgical procedures, particularly with regard to wound care, is well documented. The disclosed method and apparatus is particularly applicable with respect to use on spinal column surgeries affecting the central nervous system. However, the disclosed methods and devices may be used in other applications. As would be readily apparent to a person of ordinary skill in the art, the disclosed invention would be particularly beneficial to be used for other surgeries affecting, or in proximity to, nerve tissues other than the spinal column.

With the present invention, the apparatus comprises an ultrasound generator driving an ultrasound transducer. The ultrasound transducer can be driven at different frequency regimes such that the depth and shape of energy concentration can match the region of treatment.

An ultrasound horn is mechanically coupled to the ultrasound transducer. The ultrasound horn consists of an ultrasound tip and may also include a shaft. The ultrasound horn receives the ultrasound waves from the ultrasound generator and transmits the ultrasound waves to the distal end of the ultrasound tip either directly or through the shaft. The shaft and the ultrasound tip may be integral parts of the ultrasound horn or may be mechanically coupled as one unit. The ultrasound tip's distal portion includes a radiation surface for transmitting the ultrasound waves from the ultrasound tip to the patient's tissue.

A housing substantially encompassing the ultrasound transducer provides a hand piece for convenient holding and manipulating the device. The housing covers the ultrasound transducer and at least portions of the ultrasound horn. A shield is attached to the housing to cover at least portions of the ultrasound tip and isolate the vibrating transducer and ultrasound horn from the surgeon as well as those areas of the patient's tissue that are not intended to be undergoing treatment.

The hand piece may be provided in a variety of configurations. For example, the hand piece may be of a substantially cylindrical shape serving as a grip portion around the longitudinal axis of the ultrasound transducer, or it may be positioned to extend radially from the longitudinal axis of the ultrasound transducer serving as a grip portion having a pistol grip design.

The shield is preferably attached to the hand piece and disposed around the ultrasound tip. In one embodiment, the shield is totally independent from the ultrasound tip having an isolation gap between the ultrasound tip and the shield to prevent energy transmissions reaching the patient from portions of the ultrasound tip not being used as radiation surfaces for patient treatment.

The ultrasound tip includes a preferably a single-use disposable, non-metallic shield to prevent those vibrating concentrating elements on the tip that are not needed for the surgical treatment itself from contacting the patient's tissue. The shield is preferably made of a rigid or flexible material such as rubber, plastic, fluoropolymer or other polymer. The material is chosen so that it is sufficiently elastic so that; i) it may be installed over the wide portions of the ultrasound tip, ii) once installed it will attach to the ultrasound tip so it will not be dislodged during use, and iii) it may be easily replaced after each use. The shield may be constructed of a segmented design to facilitate installation and removal of the shield. An example of this would be having the segments substantially independent with one or more points of attachment for the segments, such as the petals of a flower. A lubricant or gel such as silicone based materials may be used to displace air between the shield and the ultrasound horn to modify the ultrasound transmission characteristics to the patient's tissue.

Ultrasound energy may be transmitted through the patient's tissue with direct contact between the radiation surface and the patient, direct contact with the shield to the patients tissue or through the use of a coupling fluid.

When a coupling fluid is used, a fluid is introduced into the ultrasound tip through a supply passage. The fluid is then transformed into a spray either within a chamber within the ultrasound tip or at the radiation surface. The spray then serves as a coupling fluid to assist the transmission of the ultrasound waves to the patient's tissue. A return passage may be used to collect and remove excess fluid that may accumulate at the treatment site.

In another embodiment, the ultrasound tip comprises on at least one radial surface, a cavity or some other form of a hollowed out area within at least one of the radial surfaces, and an edge circumventing the opening of the cavity. The edge of the cavity may be flat, sharp, jagged or rounded. In a preferred embodiment, a tapered edge or point is provided to concentrate vibrations passing through the tip. A coupling fluid is used to enhance transmission of ultrasound waves from the cavity. In this embodiment, the shield may be deformable so that the shield may normally prevent the edge from contacting tissue for easy application of ultrasound energy, but with slight pressure, the shield may be deformed to expose the cutting edge which can then be used for debridement purposes without any equipment modification such as shield replacement being required.

Ultrasound may be applied to the patients tissues by at least two mechanisms. The shield may be contacted to the tissue allowing ultrasound energy to be transferred directly from the device, such as from a radial surface or radial edge. In addition, the ultrasound energy may be focused by the cavity of the radial surface to the tissue. In this case, the coupling fluid serves as a transfer medium to allow transfer of the ultrasound waves to the tissue surface to greatly enhance the ultrasound transfer efficiency across the air interface. Typically, the focal point of the cavity is at or below the overlying tissue layer so that the therapeutic effect of the ultrasound is directed to treating the nerve tissue which are generally located below the overlying tissue.

To conduct spinal surgery requires access to the patient's tissue beneath the surface of the skin. This can be accomplished through open surgery by an incision through the skin, muscle and other tissues to access the spine. It may also by accomplished by minimally invasive techniques were the patient's tissue is accessed through skin punctures and the surgery is conducted through cannula based narrow diameter instruments, with cameras and/or other sensors being used for visualization or the surgical area.

Whether the spinal surgery is incision based or minimally invasive, the method requires having access to the patient's tissue so that the radiation surface can be placed against the patients tissue beneath the skin. Ultrasound is then applied to the nerve tissue either directly by contact with the shield or ultrasound tip or indirectly through the transmission of the ultrasound waves through the coupling fluid. Other non-neural body tissue may also serve to carry the ultrasound waves between the radiation surface of the ultrasound apparatus and the nerve tissue. For example, it may not be necessary to remove bone tissue to treat the spinal nerves within the backbone, since bone tissue may adequately transmit the ultrasound waves. Treatment may also be applied to the skin for post surgical neurological treatment or for treatment when surgery is not required.

The shield is necessary to prevent unwanted contact between the ultrasound tip and the patient's tissue. During surgery, any extended contact between the ultrasound tip and tissue could result in injury to the tissue. With regard to the radiation surface being used for treatment, the surgeon would utilize a constant motion to achieve the desired effect without injuring tissue. The shield allows other surfaces to be in a relatively stationary position in proximity to patient tissue, without the concern of tissue injury.

The proximal end of the shield may contain portions that are relatively flexible so that a edge may be easily exposed for direct contact to the patient's tissue for debridement or direct application of focused ultrasound to the tissue. This may be implemented by extending the shield beyond the perimeter of the radiation surface to maintain a gap between the shield and radiation surface, or to completely cover the radiation surface and using a shield that may have sufficient flexibility so that it may be folded back away from the radiation surface if desired by the surgeon.

Ultrasound energy may be optimized to achieve the desired effects by effectively utilizing its various properties including; thermal treatment, cavitation, microstreaming and harmonic resonance.

In combination with other effects, the intensity of the ultrasound energy may be adjusted to aid in the facilitation of neurogenesis or nerve cell repair. In combination with or in the alternative to adjusting the intensity of the ultrasound delivered, the frequency and/or amplitude of the ultrasound may be adjusted as to correspond with the harmonic resonance of different tissues as to optimize the interaction with the tissue.

Neurogenesis or the mitigation of nerve tissue injury, whether to relieve a condition that existed prior to the surgery, or to relieve damage resulting during the surgery, in this disclosure involves the application of ultrasound to the nerve cell. A nerve cell (neuron) consists of a soma, the axon and dendrites. The soma is the central portion containing the nucleus and responsible for chemical synthesis. The axon is largely responsible for the rapid transmission of information from the nerve cell to other nerve cells. Dendrites are largely responsible for the transfer of information from other neurons to the nerve cell. Information between cells occurs through synapses located at the ends of the axons and dendrites.

It has been observed that the application of ultrasound to nerve cells, initially appears to disrupt their morphology possibly stressing the cell. Following this period, the cells have been noted to exhibit regrowth. As adult neurons are not believed to divide, most likely the application of ultrasound to the nerve tissue to stimulate the nerve cells to affect regrowth through growth of axons and or dendrites. Additionally, it may be the disruption caused by the ultrasound application that stimulates neuron synapses to restore connections with other neurons.

Specifically mechanisms for repair of damaged nerve cells may include the ultrasound disrupts the natural mechanisms of the body that prevent nerve regrowth. These may include certain elements such as glial cells which form glial cell scar tissue over damaged neurons, or growth the ultrasound disruption of certain inhibiting proteins that normally prevent a nerve cell from regenerating.

Alternatively, the ultrasound may in fact stimulate the production of certain neurogenic compounds such as nerve growth factor which promotes regeneration and repair of the axon and dendrites.

One aspect of the invention is to provide methods and devices suitable for use with convention open surgical techniques.

Another aspect of the invention is to provide a method and device suitable for use with minimally invasive, cannula based surgical techniques.

Another aspect of the invention is to provide methods and devices suitable for removing non-neural tissue.

Another aspect of the invention is to provide a device with an ultrasound transducer and an ultrasound horn positioned along a similar longitudinal axis.

Another aspect of the invention is to provide methods and devices suitable for applying ultrasound to nerve tissue during surgical procedures.

Another aspect of the invention is to provide methods and devices suitable for use to stimulate nerve cell regrowth and regeneration.

Another aspect of the invention is to provide a physical barrier between portions of the ultrasound horn not being used for active treatment and the patient's tissue.

Another aspect of the invention is to prevent unintentional contact between portions of the ultrasound horn and avoid the corresponding damage to the patient's tissue.

Another aspect of the invention is to reduce ultrasound wave transmission between certain portions of the ultrasound horn and the patient's tissue.

Another aspect of the invention is to provide a shield that is deformable to expose cutting edge portions of the ultrasound horn as desired by the surgeon.

DETAILED DESCRIPTION OF THE INVENTION

Figure 1:
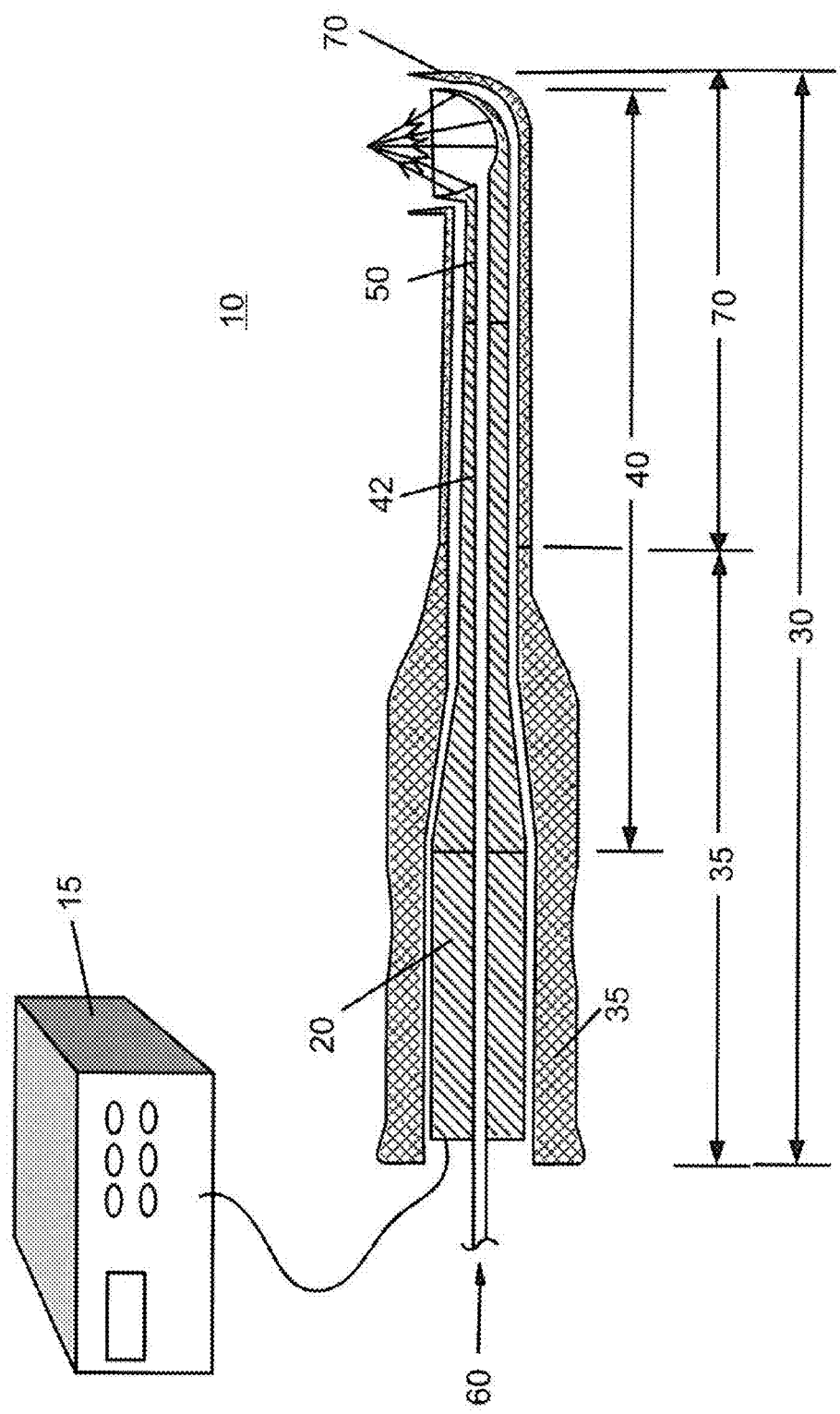
FIG. 1 depicts a cross sectional view of one embodiment of the medical apparatus with the radiation surface on a radial surface and a radial edge for cutting tissue.

The present invention is an ultrasound medical method and device for use during surgical procedures. Several embodiments and details of the invention are shown in FIGS. 1-6 and described herein. The disclosure describes the apparatus and methods in reference to spinal cord surgery on the central nervous system, however the invention is appropriate for other surgical procedures particularly on or near nerve tissue generally. The invention may be utilized to treat nerve damage that occurs before, during or after a surgery. Although examples are provided with regard to its use during surgery where access to tissue below the skin is available, the invention may also be used to treat nerve tissue through the skin when desired. FIG. 1 depicts one possible embodiment of the ultrasound apparatus 10 of the present invention. The depicted embodiment comprises an ultrasound generator 15 with an electrical cord supplying the ultrasound generator 15 its power, such as standard AC or battery power. The ultrasound generator 15 is in electrical communication with an ultrasound transducer 20 through a signal connector.

A surgeon manipulates a hand piece 30 containing an ultrasound transducer 30, a housing 35, an ultrasound horn 40 and a shield 70. The ultrasound transducer 20 is driven by the ultrasound generator 15. The housing 35 surrounds the ultrasound transducer 20 and provides a gripping surface. The housing 35 may cover portions of the ultrasound horn 40. The ultrasound horn 40 is connected to the distal end of the ultrasound transducer 20. The ultrasound horn 40 includes at least an ultrasound tip 50 and may include a shaft 42 disposed between the ultrasound tip 50 and the ultrasound transducer 20. A shield 70 preferably attached to the housing 35 covers at least portions of the ultrasound horn 40 to prevent undesirable contact between the patient's tissue and the ultrasound horn 40.

The ultrasound generator 15 and ultrasound transducer 20 are well known in the art and will not be described in detail herein. However, control of the electrical signal directly influences the ultrasound wave properties and allows optimization of the ultrasound treatment particularly with respect to the ultrasound thermal, cavitation and microstreaming properties. The ultrasound generator 15 should be capable of producing an electrical signal of a sufficient alternating voltage to drive the ultrasound transducer 20 and to achieve the desired therapeutic effect. The ultrasound transducer 20 converts the alternating voltage into mechanical motion as to induce a shaft 42 to vibrate. The shaft 42 transmits the ultrasonic vibrations to the ultrasound tip 50 to induce vibrations. For neurological treatment of nerve tissue, the amplitude of the vibrations is typically between approximately 1 micron and approximately 300 microns. The preferred amplitude range is approximately 60 microns-100 microns. The recommended amplitude value is approximately 80 microns.

For neurological treatment of nerve tissue, the electrical signal produced by ultrasound generator 15 should also be sufficient to drive the ultrasound transducer 20 to induce the ultrasound tip 50 to vibrate approximately in resonance at any frequency within the ultrasound spectrum, such as, but not limited to, between approximately 15 kHz and approximately 3 mHz. The preferred frequency range for the ultrasound tip 50 is 15 kHz to 50 kHz with a recommenced frequency of approximately 30 kHz. The ultrasound generator 15 may have multi-frequency capabilities to operate at selectable alternative frequencies within the ranged utilized.

The ultrasound transducer 20 may be driven with a continuous wave or pulsed frequency signal supplied by ultrasound generator 15. Driving transducer 20 with a continuous wave tends to induce the release of standing waves from the various surfaces of tip 50, while a pulsed frequency reduces or avoids the release of standing waves. The pulsed frequency signal generates less heat, cavitation and streaming currents, and may increase the longitudinal force of the induced vibrations as a result of the on/off cycle changes. The electrical signal may be changed depending on the desired features of the released ultrasound waves for the particular application. For example, inducing the release of standing waves may be helpful to produce or increase cavitation effects. The wave form of the electrical signal may be sinusoidal, rectangular, trapezoidal and/or triangular. In addition, the electrical signal from the ultrasound generator 15 may be fixed or modulated to allow ultrasonic wave amplitude variability. The ultrasound generator 15 may include feedback control to adjust the signal.

To conduct spinal surgery requires access to the patient's tissue beneath the surface of the skin. This can be accomplished through open surgery by an incision through the skin, muscle and other tissues to access the spine. It may also by accomplished by minimally invasive techniques were the patient's tissue is accessed through skin punctures and the surgery is conducted through cannula based narrow diameter instruments, with cameras and/or other sensors being used for visualization.

Whether for open incision surgery or minimally invasive surgery, the radiation surface 55 of the ultrasound tip 50 is typically utilized beneath a patient's skin so that ultrasound energy does not have to penetrate through the outer or subcutaneous tissue layers of the skin. In certain embodiments, a cutting edge of the device may be used to assist in tissue removal. For neurological treatment with the application of ultrasound waves, the radiation surface 50 is generally positioned so that the ultrasound radiation reaches the nerve tissue directly, or alternatively through the intervening tissue such as the back bone. Ultrasound radiation is generally applied for a duration of time from about 1 millisecond to about 30 minutes, such that the ultrasonic radiation stimulates the natural re-growth of new neurological structure and/or repair of nerve tissues. The preferred duration is from about 1 second to about 60 seconds As the surgery associated with the ultrasound therapy is typically performed under the skin layer, the shield 70 is necessary to prevent portions of the ultrasound horn 40 that are not directly involved in the treatment of the patient from contacting the patient's tissue. This is helpful in the mitigation of neurological damage and avoiding unintentional injury to non-neural tissue during the surgery from the vibrating ultrasound horn 40.

Figure 2:
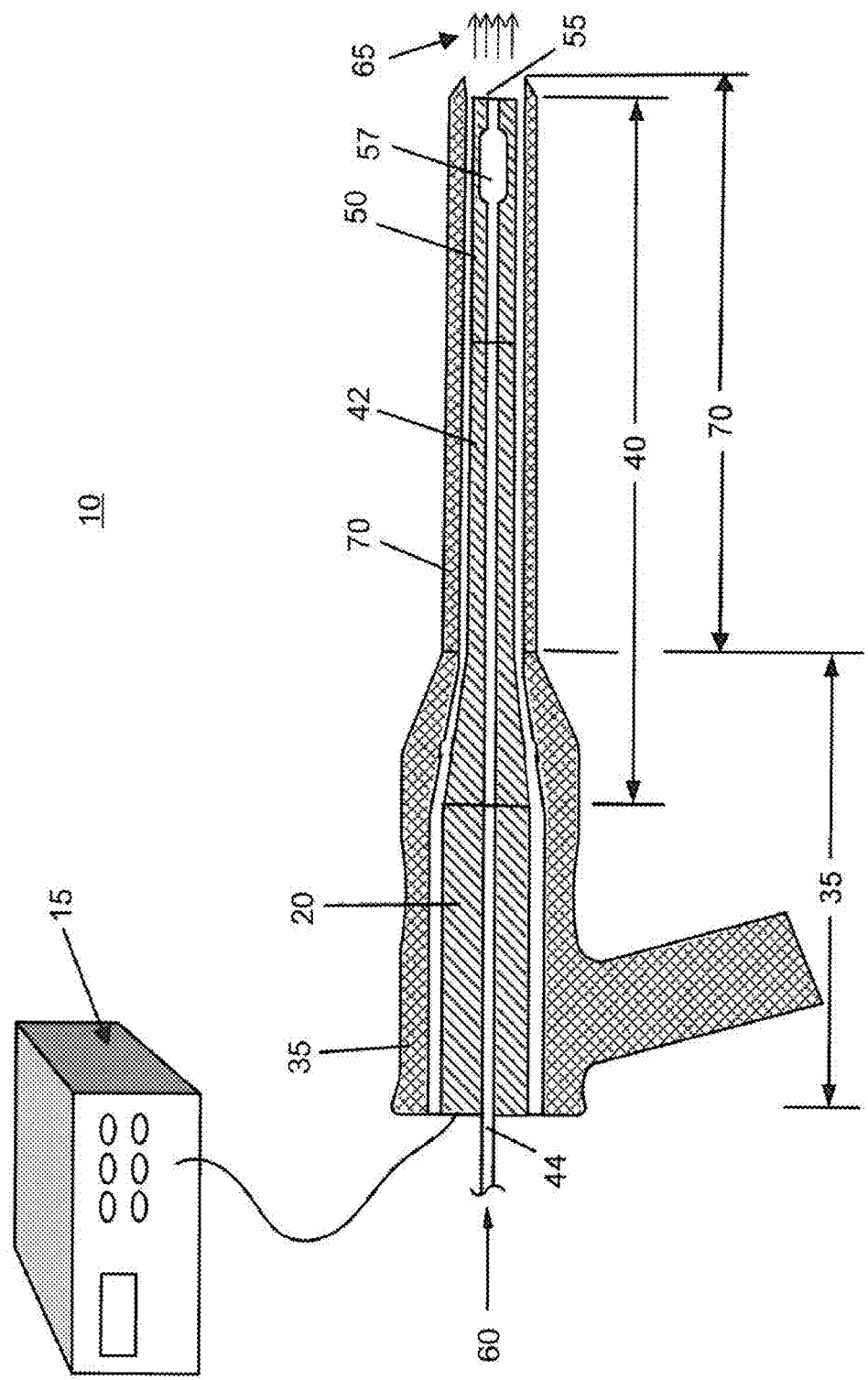
FIG. 2 depicts a cross sectional view on an embodiment of the medical apparatus with an internal chamber and a distal radiation surface for transmitting ultrasound energy.

A housing 35 serving as a handle for the ultrasound device isolates the vibrations of ultrasound transducer 20 from being transferred to the surgeon holding the device. Operators of the ultrasound device can hold the housing 35 during use to manipulate the device. The housing 35 provides a surface appropriate for hand manipulation by the surgeon and/or user while allowing the user to avoid direct contact with vibrations within the device. The housing may extend over the entire ultrasound transducer 20 and/or may partially enclose portions of the shaft 42. FIG. 1 shows a grip portion in an axial configuration. FIG. 2 shows the housing 35 incorporating a grip portion similar to a pistol grip configuration oriented radial to the longitudinal axis. The pistol grip may provide for increased visibility to the surgical site area during use of the hand piece 30.

The ultrasound horn 40 may include a shaft 42 and an ultrasound tip 50 all driven by the ultrasound transducer 20. The ultrasound tip 50 may be integral with or mechanically coupled to a shaft 42. The shaft 42 and ultrasound tip 50 connections may be completed by threading, welding and/or other means readily recognizable by people of ordinary skill in the art. The ultrasound horn 40, or portions of the ultrasound horn 40, may be removable from the hand piece for cleaning, sterilization and/or replacement as would be understood by those skilled in the art upon review of this disclosure. The shaft 42 and ultrasound tip 50 may be fabricated from metals such as, but not limited to, alloys of titanium, aluminum and/or steel.

Figure 5:
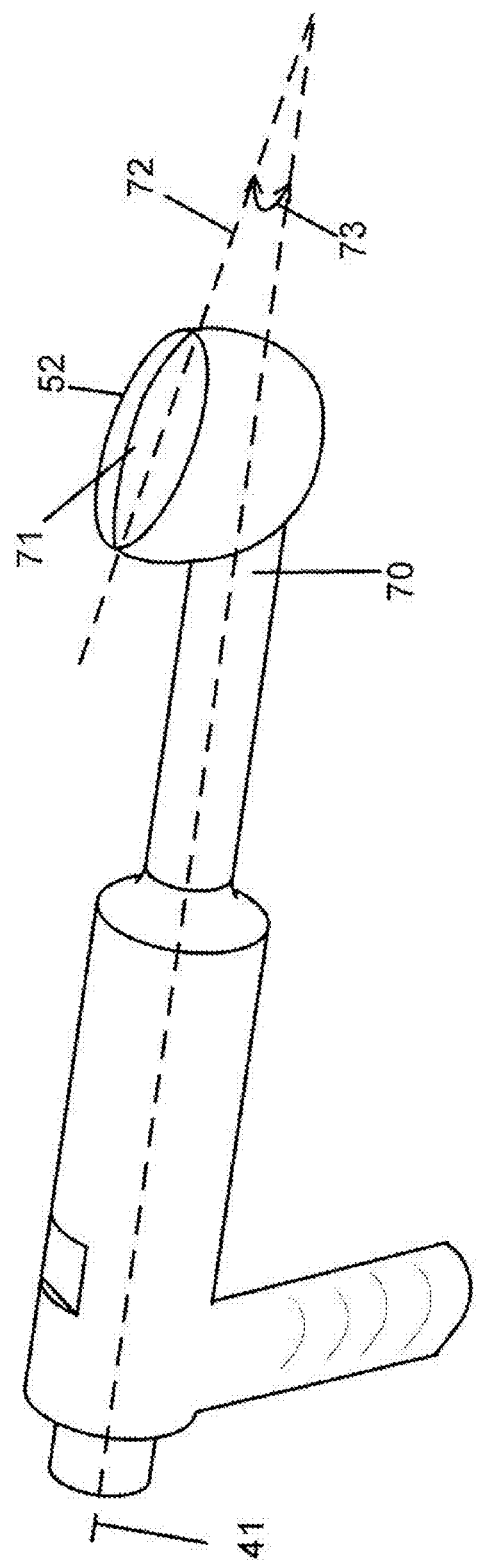
FIG. 5 depicts an alternative embodiment of the device.

As shown in FIG. 5, the shaft 42 portion of the ultrasound horn 40 may have a longitudinal axis 41. In a preferred embodiment, to prevent premature metal fatigue between the ultrasound horn 40 and the ultrasound transducer 20, the longitudinal axis 41 of the ultrasound horn is substantially co-linear with the longitudinal axis of the ultrasound transducer 20.

Figure 6:
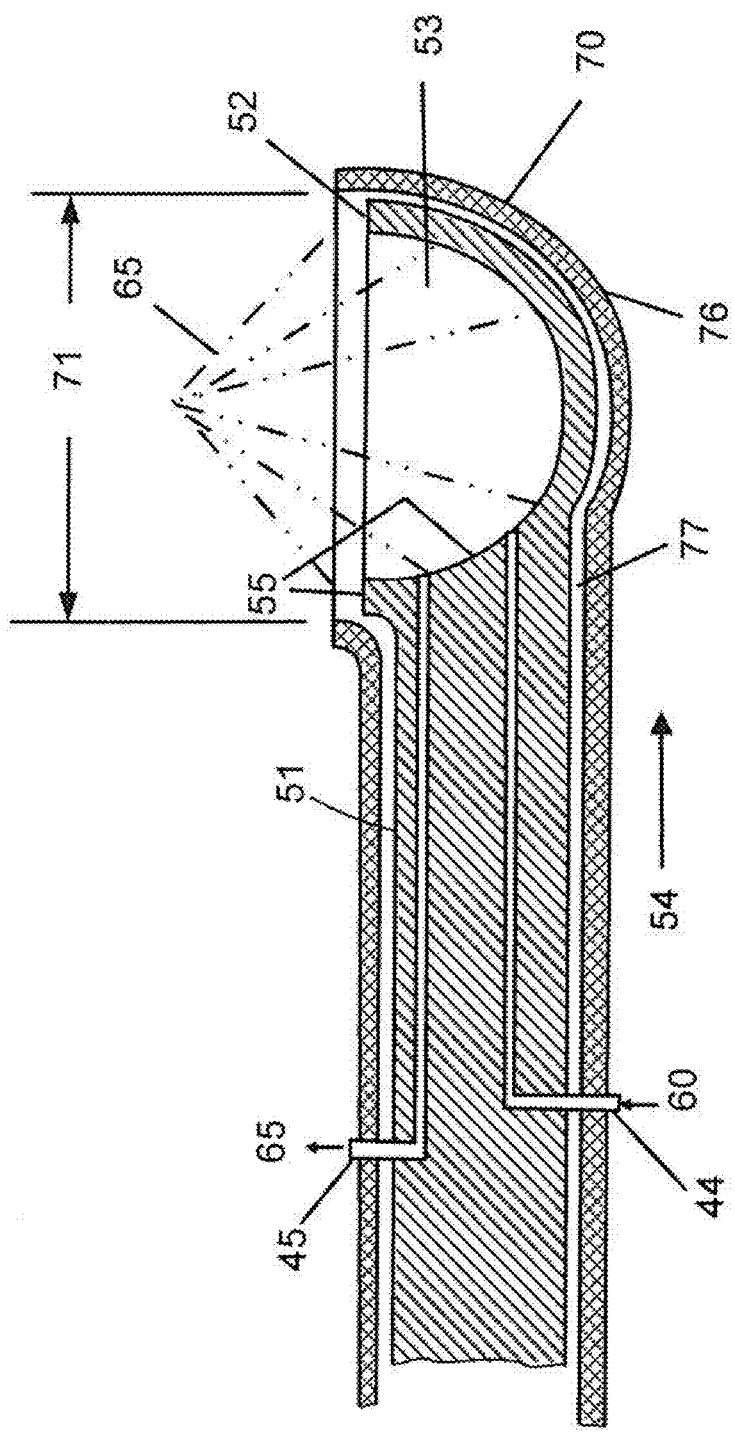
FIG. 6 depicts cross sectional view of an alternative embodiment of a shield protruding above, but not covering a flat radial edge having an isolation gap extending fully between the shield and the ultrasound tip.

As shown in FIG. 6, the ultrasound horn 40 may include at least one radial surface 51, a cavity 53 or some other form of a hollowed out area within at least one of the radial surfaces 51, and a radial edge 52 circumventing the opening of the cavity 53. The radial edge 52 may have a tapered, flat, rounded or jagged edge or at least one point to concentrate energy release along the radial edge 52.

Spinal surgery often involves decompressing a root nerve that is pinched or stabilizing a painful joint. As a surgical device, a radial edge 52 with a cutting feature may be beneficial for removing vertebrae, muscles cartilage, ligaments, joints, nerves and blood vessels associated with spinal surgeries.

The ultrasound tip 50 adjoins a non-metallic shield 70 covering those portions of the tip that would otherwise contact the patient's tissue. The shield 70 may extend past the radiation surfaces 55 to maintain a gap between the ultrasound horn 40 and the patient's tissue by shielding the radiation surface 55 from contacting the patient's tissue without covering the radiation surface 55 or blocking ultrasound transmissions. Therefore during normal use, the shield 70 prevents the metal surfaces and edges of the ultrasound tip 50 from contacting the patent's tissue and potentially damaging, for example by burning, the patient's tissue. The shield 70 does not need to cover all or any of the radial edge 52. It is sufficient for the shield 70 to maintain separation between the ultrasound tip 50 and the patient's tissue. Examples of the shield 70 simply extending beyond the lip of the radial edge 52 without actually covering it are shown in FIGS. 1, 2 and 6. The extended portion of the shield may have a terminal edge that is flat, sharp, rounded, jagged or various other configurations.

In another embodiment, the shield 70 may have an aperture 71 approximating the interior circumference of the radial edge 52 designed to at least cover portions of the radial edge 52 to prevent contact between the metal surfaces of the ultrasound tip 50 and the patient. A lubricant such as water, mineral oil or silicone gel which may be used to fill any space between the ultrasound tip 50 and the shield 70 to improve ultrasound transmissions to the patient's tissue. The shield 70 may be disposable and may be constructed of a plastic or polymer which may be formed in sections that may be releasably assembled to cover portions of the ultrasound tip 50. In a disposable embodiment, the shield 70 may be constructed to include slits between the segments to increase the deformability of the shield 70. The segments may be arranged into a geometry resembling a flower petal arrangement, fastened together at one end, such as near the aperture, for ease of installation. Preferably the shield 70 is constructed from a flexible removable material such as rubber, plastic, fluoropolymer or other polymer, so that it may be economically provided as a disposable one time use piece. Example materials include nylon, polyphenyl sulfone, polyarylamide, polyvinylchloride, polyethylene, polypropylene, PTFE, PET, PFA and PEEK™. The material is chosen so that it will maintain its position relative to the ultrasound tip 50 during use, but may be easily replaced after each use. The material needs to exhibit sufficient elasticity to stretch over the ultrasound tip 50 geometry during installation, while maintaining secure contact and conforming to the ultrasound tip during use.

Alternatively, as shown in FIGS. 2 and 6 the shield 70 may include portions of a rigid material such as a fluoropolymer, epoxy or a plastic polymer that is attached to the housing 35 forming an isolation gap 77 between the ultrasound horn 40 and the shield 70. Example materials include nylon, polyethylene, parylene, PTFE, KYNAR™, HALAR™ and XYLAN™ among others.

Ultrasound may be applied to a patient's tissue and underlying nerve tissue by at least two mechanisms. The shield 70 may be contacted directly to the tissue allowing ultrasound energy to be transferred directly from the device, for example, from a radial edge 52. Since the radial edge 52 is isolated from contacting the patient's tissue, the radial edge 52 may be sharp, jagged, flat or rounded as desired to modify the ultrasound waves transmission and associated points of concentration of the ultrasound energy transmitted from the radial edge 52. In addition, the ultrasound energy may also be focused by the cavity 53 of the radial surface 51 to the tissue. In doing this, the cavity 53 may focus the ultrasound energy with the coupling fluid 65 serving as a medium to allow transfer of the ultrasound waves to the tissue surface. Typically, the focus of the cavity 53 is external to the cavity 53, at or below the tissue layer so that the therapeutic effect of the ultrasound is directed to treating nerve tissue. Coupling fluid 65 may also serve to transmit ultrasound energy from the radial edge 52 in those embodiments having the shield 70 positioned to provide space between the radial edge 52 and the patient's tissue leaving at least portions of the radial edge 52 uncovered.

A fluid 60 is introduced to the ultrasound horn 40 through a supply passage 44. Multiple fluids 60 such as saline and oxygen may be mixed in an internal chamber 57 or at the radiation surface 55. The fluid 60 is converted to a coupling fluid 65 at the radiation surface 55. The coupling fluid 65 tends to facilitate the transmission of ultrasonic energy from the walls of the cavity 53 to the tissue to be treated. The cavity 53 may be at least partially filled with a coupling fluid 65 capable of conducting ultrasonic vibrations. The fluid 60 may include, but not limited to, saline, water, alcohol, corn oil, vegetable oil, oxygen, air or any combination thereof. When the tip is ultrasonically vibrated, cavitations may form within the coupling fluid 65 or tissue. Additionally or in the alternative, the fluid 60 within the cavity 53 may be atomized into a spray prior to reaching the radiation surface 55 and being used as a coupling fluid 65.

If a piezoelectric transducer is used to induce the substructure formed by the ultrasound horn 30, then the voltage of the electrical signal driving the transducer will largely control the degree to which the coupling fluid 65 is cavitated and/or atomized. At low voltages, the coupling fluid 65 within the cavity 53 will be cavitated to a small degree. As the voltage increases, the amount of cavitations within the coupling fluid 65 is increased. Further increasing the voltage will eventually induce atomization of the coupling fluid 65. Regardless of whether the coupling fluid 65 within the cavity 53 is quiescent, atomized and/or cavitated, the presence of a coupling fluid 65 within the cavity 53 may couple the transmission of ultrasonic energy released from the walls of the cavity 53 to the tissue to be treated. The cavity 53 may be given an initial fill of fluid 60 prior to its use. Alternatively, the fluid 60 may be continuously provided to the cavity 53 by gravity or a pump to the ultrasound tip 50 through supply passage 44 to the cavity 53.

The fluid 60 and/or coupling fluid 65 may flow along the surface of the cavity wall. Alternatively, coupling fluid 65 may leave the orifice and travel through the interior of the cavity 53 as a stream without contacting the cavity wall. Furthermore, the coupling fluid 65 may be reflected off the cavity wall and dispersed within the cavity 53. It is possible that coupling fluid 65 may be aspirated so that at least a portion is removed from the cavity 53. In any of the above alternatives the coupling fluid 65 is being directed towards the focal point(s) of the cavity 53. In addition to directing coupling fluid 65 towards the focal point of cavity 53, coupling fluid 65 may be transformed into a spray by the ultrasound energy being emitted from the interior of the cavity 53. The ultrasound waves released from the interior of the cavity 53 tend to push the spray in the direction the ultrasound waves are traveling. This direction is generally orthogonal to the surface of the cavity wall which is primarily transverse to the longitudinal axis 81 along the shaft 42 of the ultrasound horn 30. As such, the spray is directed by the ultrasound waves to the focal point of cavity 53. The ultrasonic energy carried with the coupling fluid 65 allows ultrasound waves and corresponding energy to be transferred to the patient's tissue, avoiding the relatively inefficient transmission of ultrasound energy through air. The coupling fluid 65 itself may also be used to provide a therapeutic effect at the tissue surface.

The coupling fluid 65 may also contain a therapeutic agent to enhance treatment for specific applications. An integral return passage 45 may be included in the ultrasound tip 50, with the shield 70, or between the shield 70 and the ultrasound tip 50 to serve as a component to aspirate coupling fluid 65 away from the patient after its use.

As shown in FIG. 2, the ultrasound horn 40 may include a supply passage 44 in some embodiments. The shield 70 may extend beyond the radiation surface 55 to discourage unintentional contact with the patient's tissue. The shield 70 is may be isolated from the ultrasound tip 50. Any contacts between the shield 70 may preferably be located near node points to minimize vibration transfer to the housing 35 from the transducer 20 and ultrasound horn 40.

Figure 3:
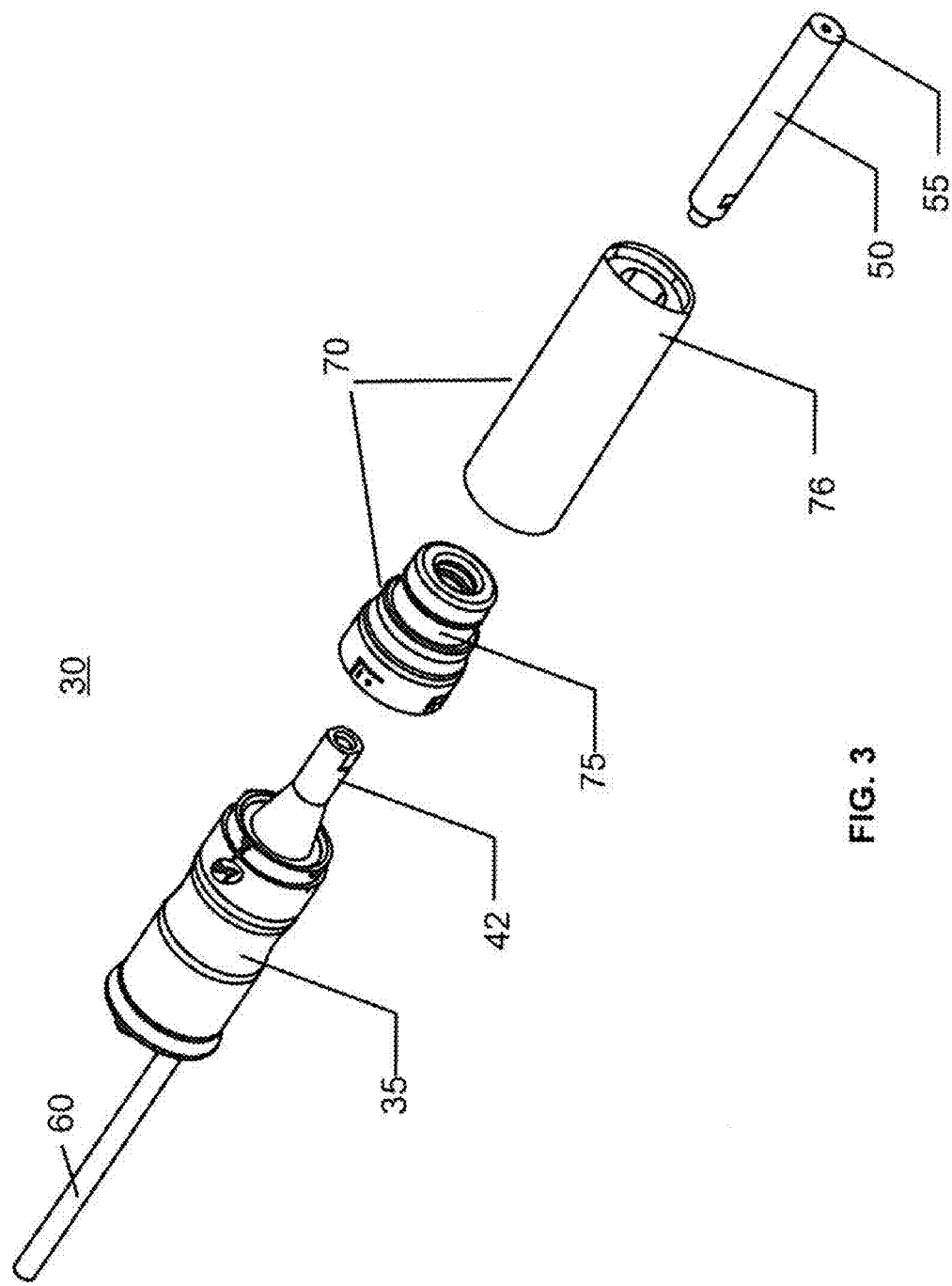
FIG. 3 depicts an exploded view of an embodiment of the apparatus with a distal radiation surface.

In FIG. 3, an exploded view of the hand piece 30 is shown. The shield 70 is shown as two pieces with a proximal end 75 and a distal end 76. Threads, O-rings, friction fit or various other attachment mechanisms may be used to attach the pieces of the shield 70 to each other as well as to the housing 35. In one embodiment the proximal end 75 may have the same hardness as the distal end 76, which may use the rigidity to help assure mechanical integrity through the attachment mechanism or may have different degrees of rigidity for the reasons described below.

In a further embodiment, the proximal end 75 and a distal end 76 may be integral with a distal end 76. In this embodiment, the units are molded as a single combined piece containing the functional characteristics of each limitation. Preferably, the proximal end 75 portion of the combined piece is cast from a material with a greater hardness than at least portions of the distal end 76. For example, the distal end 76 may have a Shore Hardness 50A or less, while the proximal end 75 may have a Shore Hardness 80A or above. This is preferred since the function of the proximal end 75 of the combined piece is to attach securely to the housing, while the function of the distal end 76 of the combined piece is to maintain flexibly while preventing the device from contacting the patient's tissue. This can be accomplished by the use of different materials in the respective portions of the unit, or utilizing other techniques such as variable curing or post production treatment of portions of the combined piece.

Figure 4:
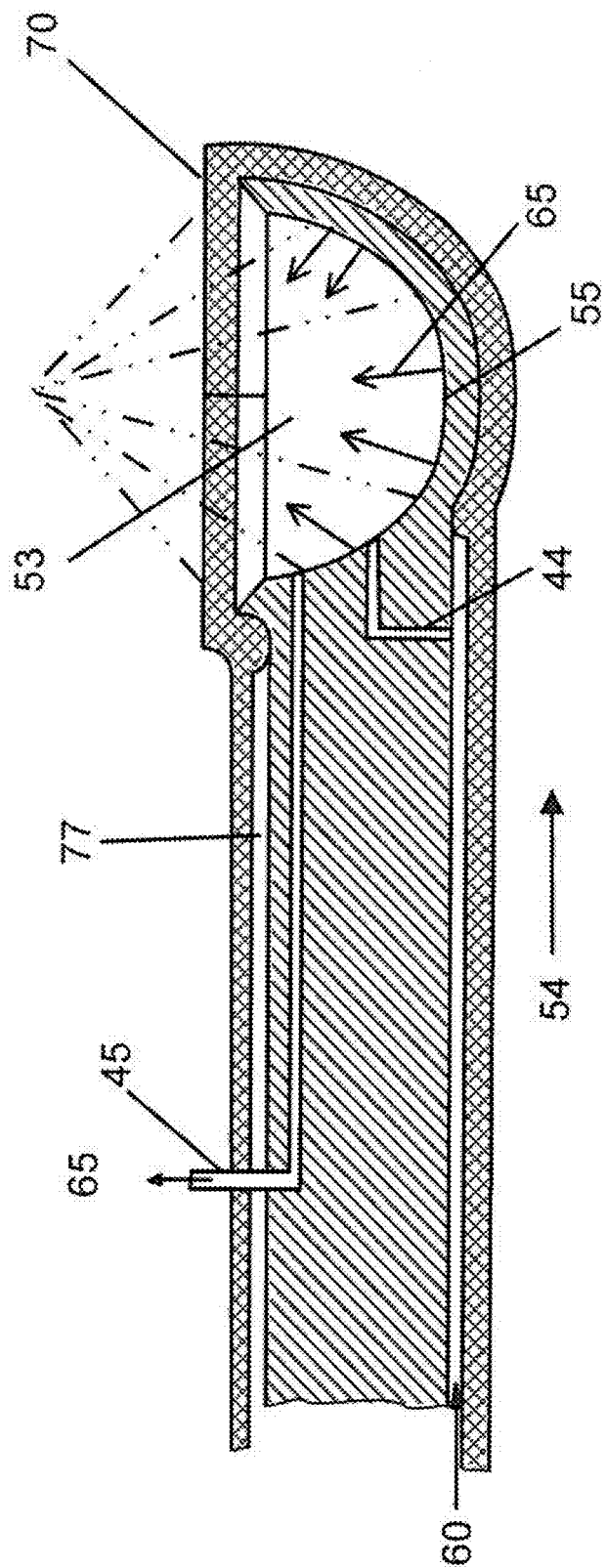
FIG. 4 depicts cross sectional view of an embodiment of a shield enclosing the ultrasound tip including the radiation surface and showing a partial isolation gap between the shield and the ultrasound tip.

FIG. 4 shows an embodiment having the cavity 53 completely covered with the shield 70 which allows maintaining substantially all of the coupling fluid 65 within the cavity 53. In this embodiment, the cavity 53 focuses the ultrasound energy, which is transmitted through the coupling fluid 65. However, the coupling fluid 65 does not contact patient's tissue and substantially all ultrasound energy passes through the shield 70 prior to reaching the patient. The coupling fluid 65 may also be removed from the ultrasound tip 50 through a return passage 45. The return passage 45 also may remove other particles and fluids from the treatment area other than coupling fluid 65. In FIG. 4 the isolation gap 77 is also used to function as the supply passage 44. The isolation gap 77 is created by allowing the shield 70 to contact a distal portion 54 of the ultrasound tip 50. The isolation gap 77 may be further segmented so that the supply passage is restricted to a narrow section of the radial surface located longitudinally to the ultrasound tip. This may be facilitated by using a flexible material, such as a silicone, to fabricate the portion of the shield 70 in contact with the ultrasound tip 50 also being helpful to minimize transfer of vibration between the radiation surface 55 and the patient's tissue.

FIG. 5 shows a further embodiment of the ultrasound horn 30 longitudinal axis 41 may be positioned to create an angle 73 with the aperature axis 72 of the aperature 71. The angle 73 may vary between 0 and 180 degrees. Preferrably the angle 73 may vary from approximately 0 to 45 degrees.

In FIG. 6, a shield 70 embodiment is shown that when installed would substantially surround the exterior surface of the ultrasound tip 50 parabolic surface with an aperature 71 external to the cavity 53 so that coupling fluid 65 may contact the patient's tissue. The segments of shield 70 may be completely independent of the ultrasound tip 50 or may be attached at portions of the adjacent ultrasound tip such as near the shield aperature 71. Fabricating the distal end 76 of the shield 70 from a resilient material allows the surgeon the flexibility of either avoiding direct contact with the patient's tissue by utilizing the rigidity of the shield 70 to maintain a gap, or to allow direct contact with the patient's tissue by folding back the free edge of the shield 70 or using some pressure against the patient's tissue to overcome the inherent rigidity of the shield 70. To dispose the shield 70 in this manner allows the shield 70 to be moveable between a position partially covering the radial edge 52 and a position allowing contact between the radial edge 52 and a patient's tissue. In another embodiment, the shield may have an internal telescoping feature so that two sections of the shield are slideable retractable to uncover the radial edge 52. The shield may be constructed as a two piece assembly, with a first piece retractable into a second piece to expose the radiation surface. The retraction feature may be, for example, a threaded interface or a slideable friction fit.

As also shown in FIG. 6 the ultrasound tip 50 receives a fluid 60, typically through a supply passage 44. Supply passage 44 may enter the ultrasound tip 50 longitudinally through the ultrasound transducer 20, shaft 42 and/or handle. An additional supply passage may be included to transfer fluid such as a therapeutic agent or cryogenic fluid to or from the ultrasound tip 50. The fluid 60 may also be delivered radially through means external to the device.

The surgeon manipulates the hand piece 30 and provide the desired therapeutic effect with the application of the ultrasound energy. Ultrasound energy may be optimized to achieve the desired effects by effectively utilizing its various properties including; thermal treatment, cavitation, microstreaming and harmonic resonance.

Central nervous system injury may occur as a condition that existed prior to the surgery such as birth defects, disease or injury. Neurogenesis or the mitigation of nerve tissue or resulting from damage during the surgery involves the application of controlled ultrasound energy to the nerve cell. A nerve cell (neuron) consists of a soma, the axon and dendrites. The soma is the central portion containing the nucleus and responsible for chemical synthesis. The axon is largely responsible for the rapid transmission of information from the nerve cell to other nerve cells. Dendrites are largely responsible for the transfer of information from other neurons to the nerve cell. Information between cells occurs through synapses located at the ends of the axons and dendrites.

In combination with other effects, the intensity of the ultrasound energy may be adjusted to aid in the facilitation of neurogenesis or nerve cell repair. In combination with or in the alternative to adjusting the intensity of the ultrasound delivered, the frequency and/or amplitude of the ultrasound may be adjusted as to correspond with the harmonic resonance of different tissues as to optimize the interaction with the tissue.

It has been observed that the application of ultrasound to nerve cells, initially appears to disrupt their morphology possibly stressing the cell. Continuous movement of the radiation surface 55 by the surgeon is necessary to avoid excessive dosages of ultrasound radiation resulting in excessive neuron damage. Even following proper dosages, some stressing of neurons has been observed. Following this initial period, the neurons have been noted to exhibit regrowth or regeneration. Adult neurons in the central nervous system are not believed to sub-divide as is typical with other cells. Therefore, the observed regeneration and regrowth is most likely due to the application of ultrasound to the nerve tissue to stimulate the nerve cells to affect regrowth through stimulation of growth of axons and or dendrites. Additionally, it may be the disruption caused by the initial ultrasound application stimulates neuron synapses to restore connections with other neurons.

Specifically mechanisms for repair of damaged nerve cells may include the ultrasound disrupts the natural mechanisms of the body that prevent nerve regrowth. It has been reported that certain elements such as glial cells form glial cell scar tissue over damaged neurons. The application of ultrasound energy may disrupt this scar tissue and allow neuron regrowth. Alternatively, the disruption of certain inhibiting proteins that normally prevent a nerve cell from regenerating may be disrupted allowing regeneration that would otherwise not be expected to occur.

Alternatively, the ultrasound may in fact stimulate the production of certain neurogenic compounds such as nerve growth factor which promotes regeneration and repair of the axon and dendrites.

Furthermore, the ultrasonic energy and/or the waves carrying it may elicit a change in the membrane permeability of deep cellular structures such as, but not limited to, axons and somas, decreasing the sensation of pain in the treated area. Additionally or in combination, the mechanical energy generated by directing ultrasound waves towards a focal point may interact with nerve cells as to provide an analgesic effect.

The cavitation of coupling fluid 65, as well as the mechanical energy associated with the focused ultrasound energy can be used to assist the production of ozone from the oxygen associated with the air and/or liquid. The ozone produced may be utilized to assist the ultrasound energy to disrupt cellular materials and inactive pathogens. Thereby, the ozone may provide therapeutic disinfecting properties to help the patient resist infections.

Although specific embodiments of apparatuses and methods using the treatment of the spinal cord central nervous system as an example, have been illustrated and described herein, it will be appreciated by those of ordinary skill in the art that any arrangement, combination, and/or sequence that is calculated to achieve the same purpose may be substituted for the specific embodiments shown. It is to be understood that the above description is intended to be illustrative and not restrictive. Combinations of the above embodiments and other embodiments as wells as combinations and sequences of the above methods and other methods of use will be apparent to individuals possessing skill in the art upon review of the present disclosure.

The scope of the claimed apparatus and methods should be determined with reference to the appended claims, along with the full scope of equivalents to which such claims are entitled.

I claim:

1. An ultrasound apparatus for use in spinal surgery comprising:
   an ultrasound generator capable of driving an ultrasound transducer;
   an ultrasound horn attached to the ultrasound transducer, the ultrasound horn having an ultrasound tip having a radiation surface containing a cavity configured to focus ultrasound energy at an ultrasound tip distal end, a shield at least partially surrounding the ultrasound tip configured to prevent contact between the radiation surface and a patient's tissue, and an isolation gap between at least a portion of the ultrasound tip and the shield;
   the cavity also containing a coupling fluid;
   the ultrasound tip also having a radial edge circumventing the cavity.

2. The ultrasound apparatus of claim 1 wherein the shield is moveable between a position partially covering the radial edge and a position allowing contact between the radial edge and a patient's tissue.

3. The apparatus according to claim 1 wherein the ultrasound horn also has a supply passage for transferring the coupling fluid to the cavity.

4. The apparatus according to claim 1 the ultrasound generator capable of producing an electrical signal of a voltage sufficient to induce cavitations within the coupling fluid.

5. The apparatus according to claim 1 characterized by the ultrasound generator being capable of producing an electrical signal of a voltage sufficient to atomize the coupling fluid.

6. The apparatus according to claim 1 wherein the ultrasound transducer receives a modulated signal.

7. The apparatus according to claim 1 characterized by the ultrasound transducer being capable of inducing the ultrasound horn to vibrate approximately in resonance at a frequency between approximately 15 kHz and approximately 3 mHz.

8. The apparatus according to claim 1 characterized by the ultrasound transducer being capable of inducing the ultrasound horn to vibrate approximately in resonance at a frequency of approximately 30 kHz.

9. The apparatus according to claim 1 producing an electrical signal of a voltage sufficient to induce the ultrasound horn to vibrate approximately in resonance having a plurality of vibrations with an amplitude being between approximately 1 micron and approximately 100 microns.

10. The apparatus according to claim 1 wherein the the ultrasound generator capable of producing an electrical signal of a voltage sufficient to induce the ultrasound horn to vibrate approximately in resonance having a plurality of vibrations with an amplitude being approximately 80 microns.

11. The apparatus of claim 1 wherein the shield completely encloses a cavity opening.

12. The apparatus of claim 1 wherein a longitudinal axis of the ultrasound tip and a longitudinal axis of the ultrasound transducer are substantially co-linear.

13. The apparatus of claim 1 further comprising, a housing substantially encompassing the ultrasound transducer wherein the housing has a grip portion having a substantially axial configuration along a longitudinal axis.

14. The apparatus of claim 1 further comprising, a housing substantially encompassing the ultrasound transducer wherein the housing has a grip portion in an pistol grip configuration radial to a longitudinal axis.

15. An ultrasound apparatus for use in spinal surgery comprising:
   an ultrasound generator driving an ultrasound transducer;
   an ultrasound horn attached to the ultrasound transducer;
   the ultrasound horn having a chamber for mixing a fluid;
   a radiation surface at an ultrasound horn distal end;
   a housing substantially encompassing the ultrasound transducer in addition to at least portions of the ultrasound horn;
   a shield attached to the housing at least partially covering the ultrasound horn and configured to prevent contact between the radiation surface and a patient's tissue.

* * * * *